United States Patent [19]

Uemura

[11] Patent Number: 4,484,584
[45] Date of Patent: Nov. 27, 1984

[54] METHOD AND APPARATUS FOR BLOOD PRESSURE MEASUREMENT

[75] Inventor: Masahiro Uemura, Komaki, Japan

[73] Assignee: Nippon Colin Co., Ltd., Komaki, Japan

[21] Appl. No.: 346,769

[22] Filed: Feb. 8, 1982

[51] Int. Cl.³ ............................................. A61B 5/02
[52] U.S. Cl. .................................. 128/680; 128/681
[58] Field of Search ............................ 128/680–683; 346/33 ME

[56] References Cited

U.S. PATENT DOCUMENTS

| 2,447,018 | 8/1948 | Keinath | 346/33 ME X |
| 3,146,777 | 9/1964 | Lee | 346/33 ME |
| 4,105,021 | 8/1978 | Williams et al. | 128/683 |
| 4,144,879 | 3/1979 | Nakayama et al. | 128/680 |

Primary Examiner—Kyle L. Howell
Assistant Examiner—Francis J. Jaworski
Attorney, Agent, or Firm—Browdy and Neimark

[57] ABSTRACT

Blood pressure measuring method and an apparatus applicable therefor, wherein a graph indicating the relation between pressure in a cuff which is variable in the measurement process and magnitude of pulse waves generated from a part of a human body under the pressure of the cuff is described, and a mark is given for indicating the cuff pressure at a blood pressure measuring point on to the graph, for allowing judgement whether the measured data are appropriate or not by comparison of the distribution condition of the magnitude of the pulse waves and the position of the mark. Even when noises difficult to be discriminated in the circuit only should be mingled into the pulse waves so as to automatically proceed the measurement, the erroneous measurement caused by the noises can be judged by the above comparison so that the error data can be excluded or cancelled.

11 Claims, 10 Drawing Figures

METHOD AND APPARATUS FOR BLOOD PRESSURE MEASUREMENT

BACKGROUND OF THE INVENTION

This invention relates to a method and an apparatus to realize the same for automatically measuring blood pressure and for estimating the propriety or exactness of the actually measured data.

As automatic blood pressure apparatuses belonging to this category, one wherein blood pressure is automatically measured by means of detecting KOROTKOFF SOUND (hereinafter will be abbreviated as K. S.) to be contained in the pulse wave sound according to pressure variation in a cuff wound around a human upper arm, and another based on the oscillometric method wherein blood pressure is automatically measured by means of detecting variation of pressure oscillation taking place in a cuff according to the pulse wave can be numerated as a couple of main propositions. In those apparatuses accidental mingling of noises, such as so-called MOTION ARTIFACT which may be produced when the body of a subject is moved, into the K. S. or the pressure oscillation may cause, in case of the noises being quite near in the frequency and the generation timing thereof to either object to be detected, difficulty of discrimination of the mingle and detecting the targeted the K. S. or pressure oscillation, which inevitably results in an automatic mismeasuring of the blood pressure.

SUMMARY OF THE INVENTION

The primary object of this invention, which was made from such a background, is to provide a blood pressure measurement method and an apparatus therefor, wherein high reliability can be maintained in the obtained data due to the capability of pointing out the inappropriateness of the data if any noises such as MOTION ARTIFACT should mingle into the measurement process.

For achieving the above-mentioned object the inventive blood pressure measuring method includes the following steps: measuring a maximum blood pressure value (SYSTOLIC PRESSURE) and a minimum blood pressure value (DIASTOLIC PRESSURE) by detecting pressure in a cuff, in which inner pressure is variable, and pulse wave in a blood vessel under compression of the cuff; indicating magnitude of the pulse wave variable according to the variation of pressure in the cuff on a two-dimensional graph constituted of a pressure axis which takes the cuff pressure as a variable and a pulse wave axis which takes the magnitude of the pulse wave as a variable; indicating distribution of the magnitude of the pulse wave corresponding to the variation of the cuff pressure in the graph; and attaching a mark, respectively designating pressure value of the cuff when the maximum blood pressure value and the minimum blood pressure value have respectively been measured, to the graph.

And the invented blood pressure measuring apparatus, for realizing the above-mentioned method, which is provided with a pressure detector for detecting pressure in a cuff in which inner pressure is variable and outputting a pressure signal representing the detected pressure and a pulse wave detector for detecting pulse wave of a blood vessel under compression of the cuff and outputting a pulse wave signal representing the pulse wave, for automatically measuring a maximum blood pressure value and a minimum blood pressure value based on the pressure signal and the pulse wave signal, characteristically comprises: a peak hold circuit for maintaining a peak value of the wave form of the pulse wave; a memory for storing the peak value and pressure value of the cuff represented by the pressure values synchronously with generation of the pulse wave signal; an output means for displaying a two-dimensional graph which includes a pressure axis taking the cuff pressure as a variable and a pulse wave axis indicating the peak value; and a data processing circuit for controlling, based on the peak value and the cuff pressure value stored in the memory, the output means so that distribution of the peak value corresponding to variation of the cuff pressure may be displayed on the two-dimensional graph, and a mark representing respective pressure value of the cuff when the maximum blood pressure value and the minimum blood pressure value have been measured are put to the graph.

By means of such a structure the obtained data from the blood pressure measuring can be easily judged as to whether it is appropriate and exact for the diagnosis purpose through comparison of the distribution of magnitude of the pulse wave corresponding to pressure variation in the cuff and the marks representing the S. P. and the D. P. And data of the blood pressure disturbed by noises difficult to discriminate can therefore be easily cancelled. This apparatus greatly contributes the provision of highly reliable measurement data in the event of automatic blood pressure measuring for a pro-operation patient who has to be observed for a long time continuously and particularly when he/she must be observed continuously in respect of timewise varying trend.

BRIEF DESCRIPTION OF THE DRAWING

FIGS. 6 and 7 are respectively an indication of data output on a sheet of printer, in which:

DETAILED DESCRIPTION OF THE PREFERRED EMBODIMENT

Figure 1:
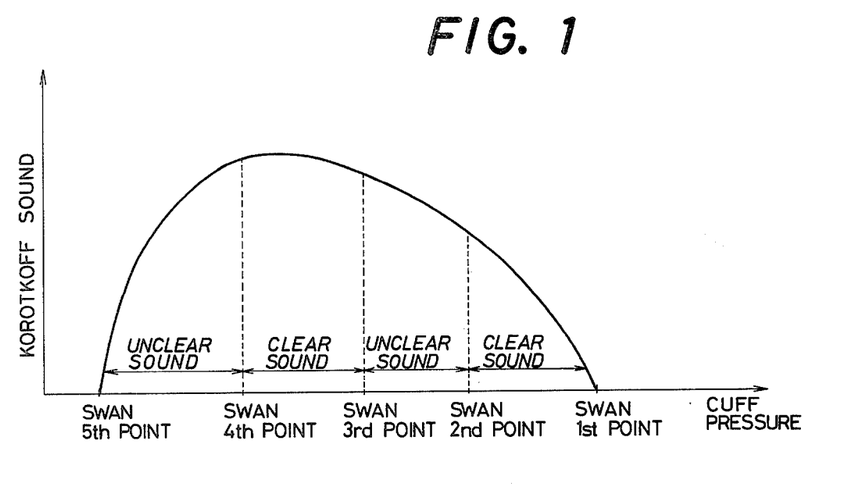
FIG. 1 is a graph showing the general property of the K. S. appearing condition.
Figure 8:
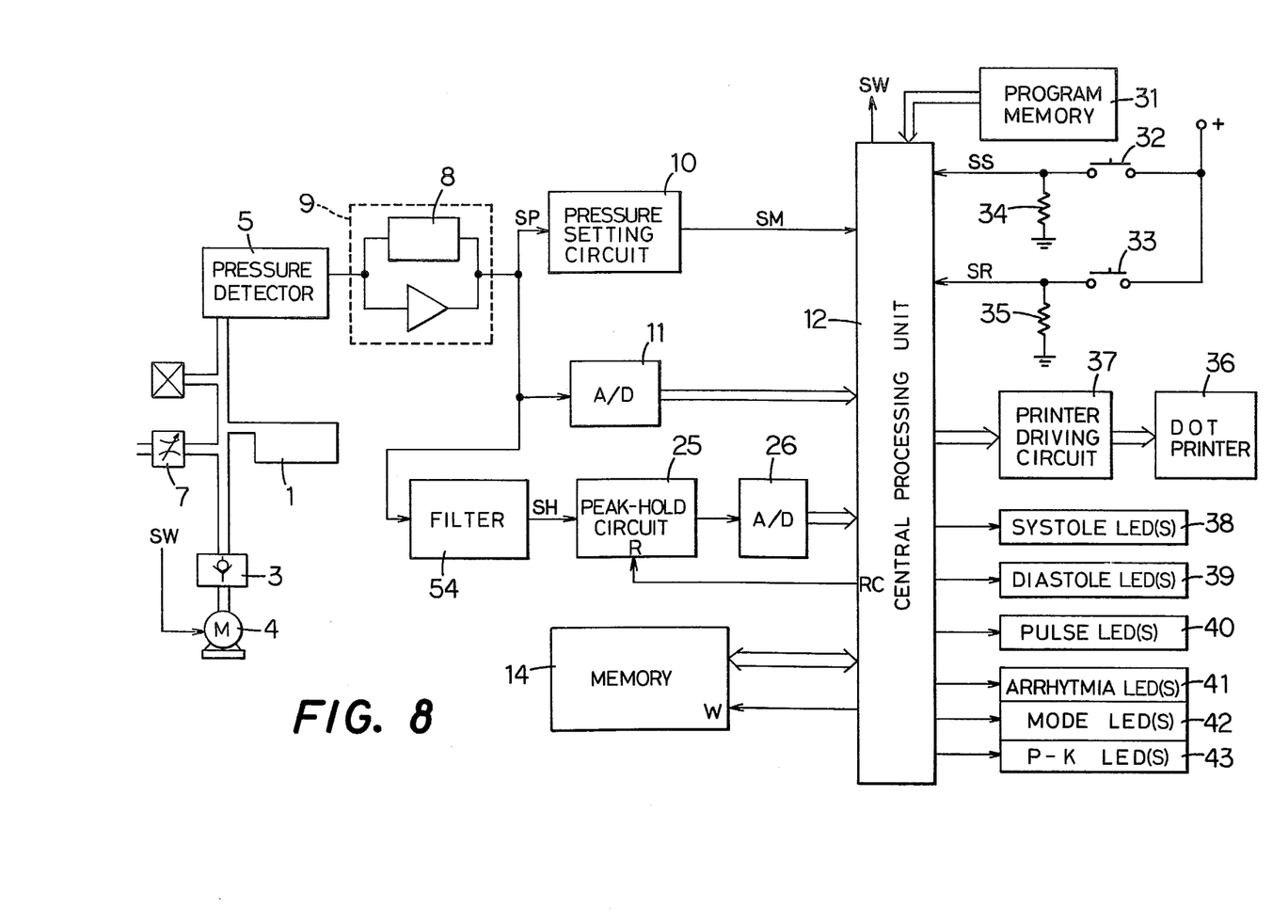
FIG. 8 is a block diagram showing the structure of another embodiment of this invention.

A cuff, which is designated with numeral 1 in FIGS. 2 and 8 in the drawing, and KOROTKOFF SOUNDs, which are generated from a part of a human body where the cuff, applies pressure, stand in the following relation. When the value of the pressure detected by the cuff 1 is gradually decreased as shown in FIG. 1, the blood begins to flow through the hitherto pressed portion of the blood vessel in synchronization of the heart contraction, generating the K. S. This point of pressure, where the K. S. is initiated, is called a SWAN first point. The K.S. grows larger corresponding to the decrease of the cuff pressure. It is however diminished, according to the pressure flowing onto the blood vessel because of lack of friction between the blood vessel and the blood flow, starting at a SWAN fourth point, and finally disappears at a SWAN fifth point. The K. S. are generated thus collectively but consecutively, and a line linking distributed peak points describes a gentle envelope curve. By the detection of the SWAN first point and the SWAN fifth point the S. P. and the D. P. are substantially determined. And a SWAN second point and the SWAN fourth point respectively constitute a turning point where the K. S. is turned from a clear sound to a voiced or unclear sound; a SWAN third point constitutes a border line from a voiced sound to a clear sound.

Figure 2:
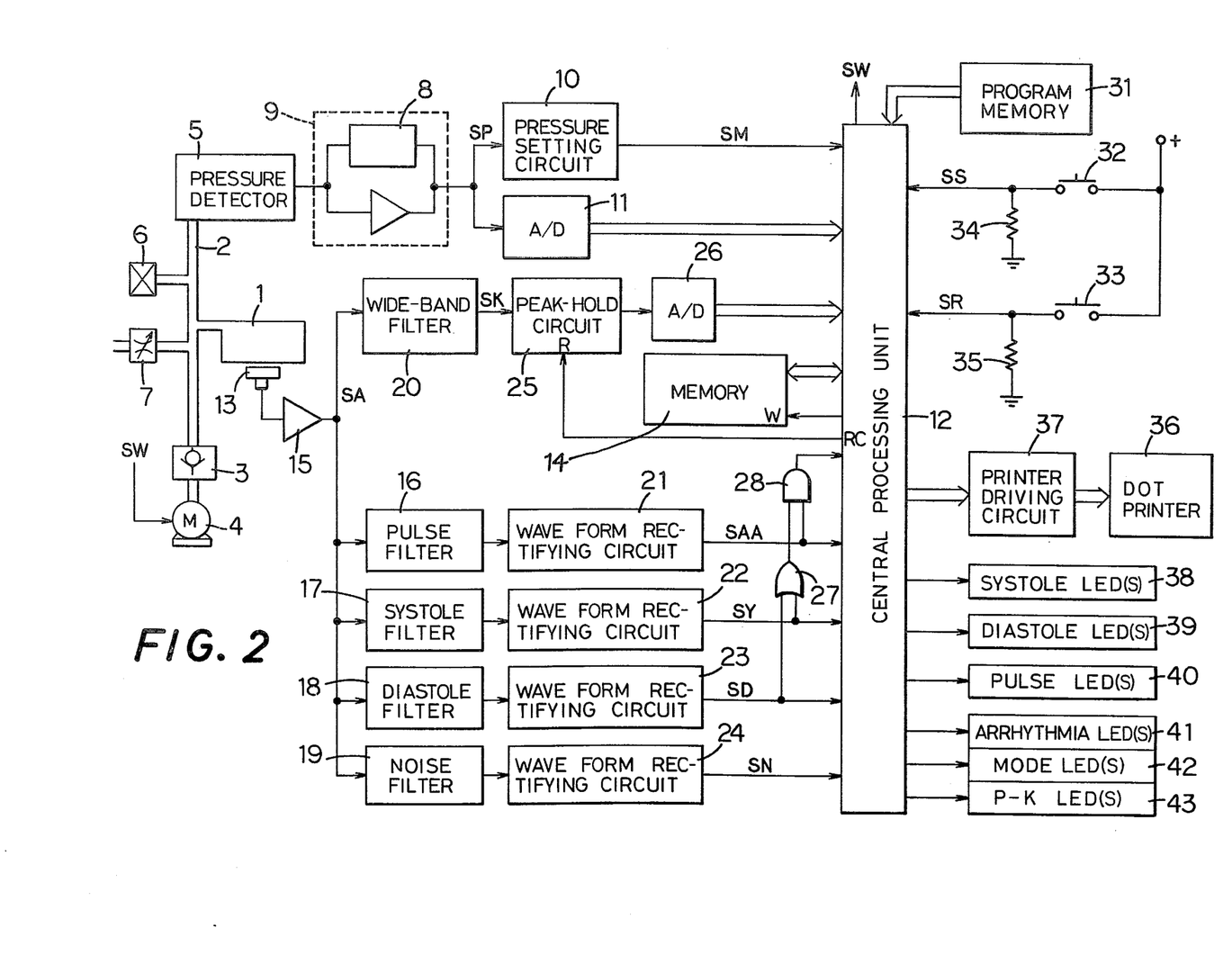
FIG. 2 is a block diagram showing the structure of an embodiment of this invention.
Figure 3:
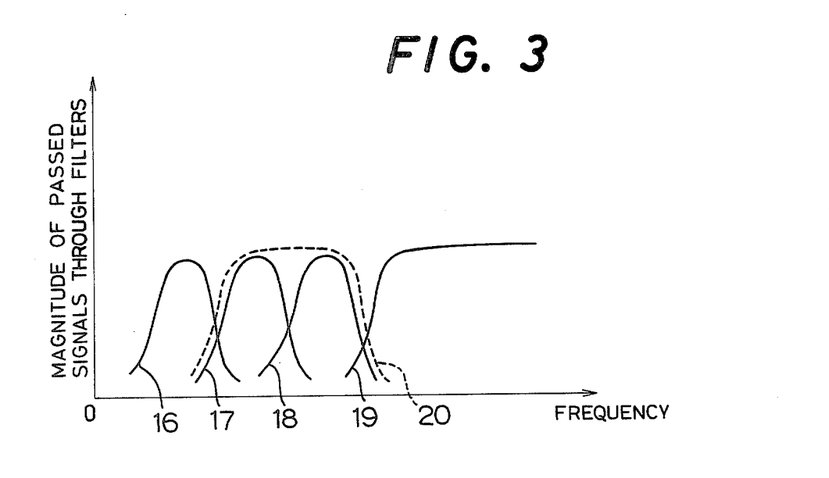
FIG. 3 is a graph showing the characteristics of a filter employed in the embodiment in FIG. 2.

To the cuff 1, as shown in FIG. 2, a tube 2 is connected, and to one end of the tube 2 an air pump 4 is connected by way of a check value 3, which restricts the flow amount toward the air pump 4. On the other end of the tube 2 an ordinary pressure detector 5 for detecting the pressure value in the cuff 1 and outputting a pressure signal SP, an electric signal representing the detected pressure value, is connected. In the middle portion of the tube 2 an electromagnetic valve 6 for rapid air discharge and a throttle valve 7 for gradual air discharge are disposed.

The pressure signal SP is supplied, after having been amplified by an amplifier 9 provided with a zero-point compensation circuit 8, to a pressure setting circuit 10 and an A/D converter 11. The pressure setting circuit 10 is an ordinary comparator circuit wherein when the input pressure signal SP exceeds a voltage value representing the maximum pressure value of the cuff 1 (about 150 mmHg-200 mmHg) a pump-stopping signal SM is generated. This pressure setting can be made by a not-shown potentiometer at a predetermined value. The signal SM is supplied to a central processing unit (CPU) 12. The A/D converter 11 functions to convert an analogue signal into a digital signal, so that the pressure signal SP is changed to a digital signal for being supplied to a memory 14 by way of the CPU 12. The memory 14 is made up of an ordinary random access memory (RAM), functioning for storing the pressure signal SP and a later described peak value of the K. S. and at the same time as a working memory for the CPU 12.

In the cuff 1 a microphone 13 is disposed in a closely fittable status to a human arm, as a pulse wave sound detector for detecting the pulse wave sound intermittently generated in the blood vessel. The pulse wave sound generated in the pressed or compressed blood vessel by the cuff 1 is, upon having been detected by the microphone 13, converted to a pulse wave sound signal SA as an electric signal. The signal SA is then supplied via an amplifier 15 to a pulse filter 16, a systole filter 17, a diastole filter 18, a noise filter 19, and a wide-band filter 20.

To the pulse wave sound signal SA a K. S. generated by the friction between the blood vessel and the blood flow when the blood vessel is pressed by the cuff 1, a MOTION ARTIFACT above-mentioned, and other noises may be included, in addition to the pulse applied to the blood vessel from the heart. The earlier mentioned filters 16-20 function herewith to separate a pulse signal SAA, a K. S. signal SK, a noise signal SN, diastole sound signal SD, and a systole sound signal SY from the pulse wave sound signal SA, with respective feature of passing specific frequency. Although the diastole sound signal SD and the systole sound signal SY are generally included or embraced in the K. S. signal SK in regard to their frequency, the frequency components of the K. S. signal SK, are somewhat different only at the SWAN first point and the SWAN fifth point from those in the other points. So the diastole sound signal SD and the systole sound signal SY can be respectively separated for being utilized to the blood pressure measurement as highly reliable data.

The pulse signal SAA, the systole sound signal SY, the diastole sound signal SD, and the noise signal output SN from the filters 16-19 are respectively rectified in wave-form rectifying circuits 21-24 into pulse form before being supplied to the CPU 12. The K. S. signal SK output from the wide-band filter 20 is supplied to a peak-hold circuit 25, which is an ordinary peak maintaining circuit for maintaining the maximum value of the signal SK, which represents the magnitude of the wave thereof, so as to continue outputting of the maximum value to the A/D converter 26 intil a result terminal R of circuit 25 receives a signal input. The A/D converter 26 converts the peak value as an analogue signal to a digital signal before supplying it to the memory 14 via the CPU 12.

For storing the peak value of the signal SK at the time of generation of the K. S. signal SK and the pressure signal SP at this time in the momory 14 an output terminal of wave-form rectifying circuits 22, 23 is respectively connected to an input terminal of an OR circuit 27, and an output terminal of the OR circuit 27 and an output terminal of a wave-form rectifying circuit 21 are respectively connected to an input terminal of an AND circuit 28. An output signal from the AND circuit 28 is applied via the CPU 12 to an input terminal W for writing of the memory 14, and an output terminal RC of the CPU 12 is connected to a reset terminal R of the peak-hold circuit 25 for resetting the same after completion of writing in the memory 14.

Figure 4:
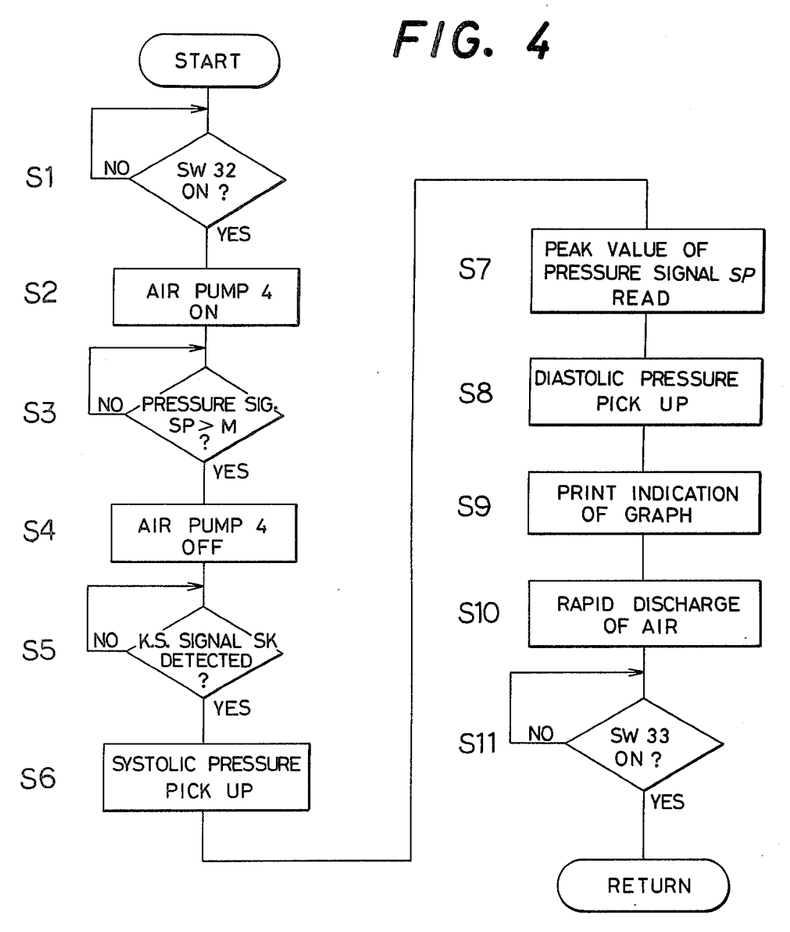
FIG. 4 is a flow chart in respect of the embodiment in FIG. 2.

The CPU 12 is provided with a program memory 31 for accommodating a program shown in FIG. 4 which prescribes the signal processing to be performed in the CPU 12, a starting switch push button 32 for supplying a start signal SS to start the program, and a resetting switch push button 33 for supplying a reset signal SR to restore the program to its original status. Besides, numerals 34 and 35 designate respective pulldown resistors.

The CPU 12 is further provided with output means such as a printer driving circuit 37 and a dot-printer 36, the former supplying a drive signal to the latter according to a received signal from the CPU 12 and the latter printing numerals, letters, and graphs under the command of the drive signal. Besides, the CPU 12 further includes LEDs 38-43 for visibly indicating the output of various signals by illuminating lamps.

A systole LED(s) 38, a diastole LED(s) 39, and a pulse LED(s) 40 are respectively an illuminated indication in response to the generation of the systole sound signal SY, the diastole sound signal SD, and the pulse signal SAA. An arrhythmia LED(s) 41 is illuminated when the pulse signal SAA fluctuates in its cycle exceeding a certain predetermined rate; and a mode LED(s) 42 is for indicating the operation status of the blood pressure measuring apparatus such as AUTO- MATIC, BLIND, etc. Finally a P-K LED(s) 43 is for indicating the generating condition of the pulse signal SAA and the K. S. signal SK by a blue lamp and a red lamp.

Operation of the blood pressure measuring apparatus of such a structure will be described hereunder with reference to FIG. 4.

First of all steps S1–S4 are performed, specifically speaking:

When the starting switch push button 32 is depressed, with the cuff 1 being wound about an upper arm of a subject person, a start signal SS is supplied to the CPU 12 for actuating the air pump 4. Pressure in the cuff 1 is therefore raised so as to press the upper arm, finally blocking the blood flow. When the pressure signal SP supplied from the pressure detector 5 by way of the amplifier 9 exceeds the predetermined maximum pressure value M (approx. 150 mmHg) a pump stopping signal SM is supplied from the pressure setting circuit 10 to the CPU 12, which suspends outputting of the hitherto supplied drive signal SW of the CPU 12 so as to stop the air pump 4. Ceasing of pressure rising in the cuff 1 taking place in this way will cause the pressure to be gradually lowered due to discharging of the air through the throttle value 7, as can be seen in the graph of FIG. 5 indicating a timewise trend of the cuff pressure value.

Before proceeding to the next stage, filtering, wave rectifying, and other necessary operations for better understanding will be explained here in advance.

Figure 5:
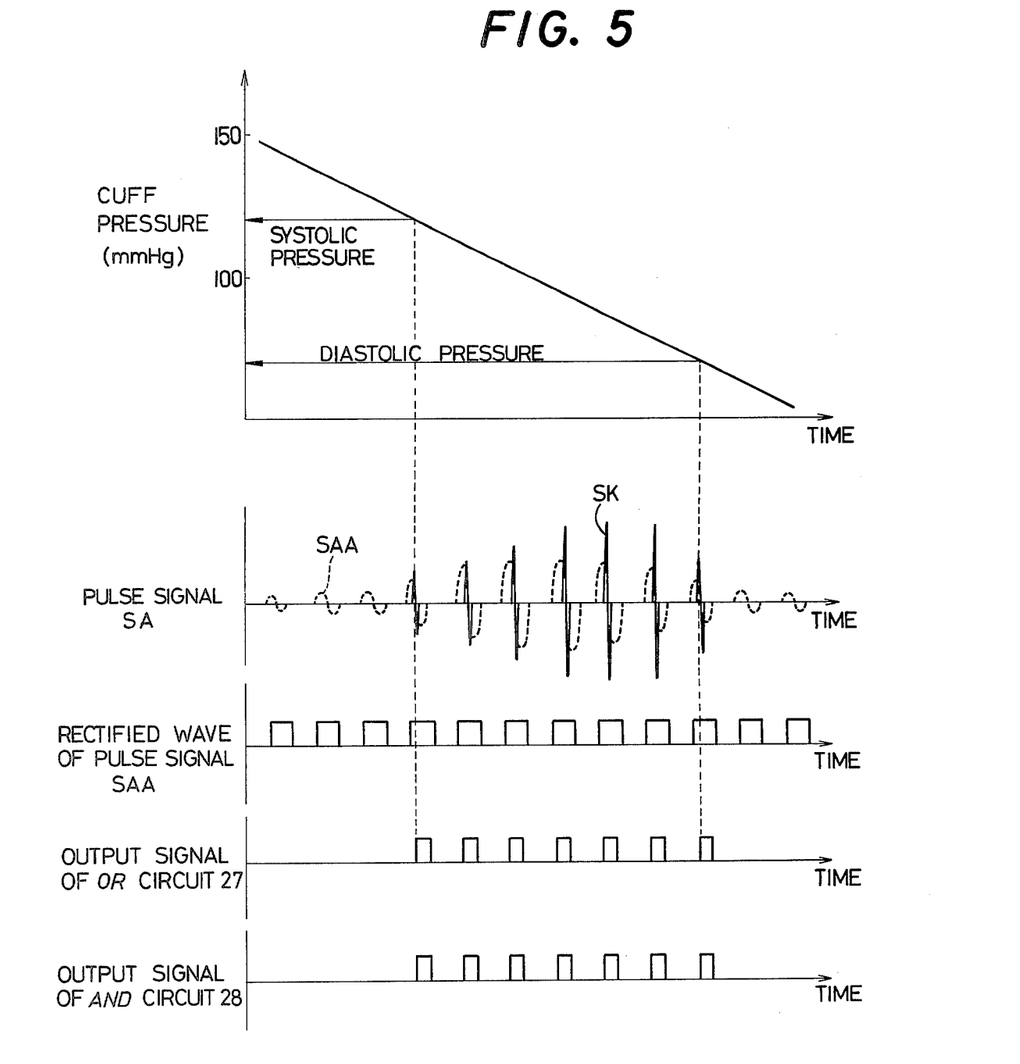
FIG. 5 is an operation explaining graph in respect of the embodiment in FIG. 2.

The pulse wave sound signal SA including the pulse signal SAA, a broken line wave in FIG. 5, and the K. S. signal SK, a solid line wave, is detected in the course of the pressure lowering as can be seen in an illustrated pulse wave sound signal SA in FIG. 5 by a microphone 13. The pulse signal SAA representing only true pulses can be then separated from the pulse wave sound signal SA by the filter 16 to be taken out for being wave rectified into the pulse form wave. The K. S. signal SK is separated synchronously with generation of the K. S. by the filter 20 for being supplied to the peak-hold circuit 25, wherein the peak value thereof is kept there. On the other hand, the systole sound signal SY and the diastole sound signal SD are respectively separated by the filter 22 and the filter 23 for being wave rectified. Output signals from the OR circuit 27 and the AND circuit 28 representing generation of the K. S. appear therefore in the form illustrated in FIG. 5. The output signal from the AND circuit 28 is supplied in synchronization with the generation of the K. S. to the memory 14, via the CPU 12, for making the same memorize the above-mentioned peak value and the pressure signal SP representing the then pressure in the cuff 1, and further making the peak hold circuit 25 which receives a signal after a certain time from the output terminal RC of the CPU 12 to be reset at the peak hold status in preparation for the next peak hold wave form. The just mentioned process of operation is repeated until the K. S. disappears. When noises having frequencies above a certain limit are included in the pulse wave sound signal SA, and when the noise signals are separated by the noise filter 19, in putting of the K. S. signal SK, the systole sound signal SY, the diastole sound signal SD, and the pulse signal SAA at this time is automatically cancelled for preventing misoperation of the apparatus. Besides, the AND circuit 28 also functions to exclude or remove, even when some noises with a near frequency to that of the K. S. escaping the separation by the noise filter 19 are mingled by chance, the noises during the absence of the pulse signals SAA.

Figure 6:
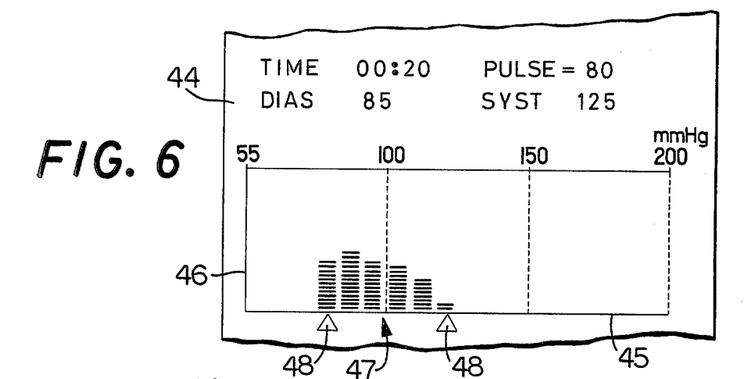
FIG. 6 indicates a normal status.

Secondly, steps S5–S9 are performed herewith:

The CPU 12 functions to discriminate, according to the program stored in the memory 14, the foremost and the rearmost of the continuously produced KOROTKOFF SOUNDs (at least either one of the systole sound signal SY or the diastole sound signal SD) for determining the SYSTOLIC PRESSURE and the DIASTOLIC PRESSURE by means of picking up the pressure of the cuff 1 represented in the form of the pressure signal SP at the time of generation of those K. S. Number of pulsations per minute can be calculated based on the input cycle of the pulse signals SAA, and visible indication of such data in combination with the SYSTOLIC PRESSURE, DIASTOLIC PRESSURE, and the time of the measurement is printed on a paper tape 44 in the dot printer 36 shown in FIG. 6. At the same time a two-dimensional graph 47 is printed on the paper tape 44, in which graph a pressure axis 45 constitutes the abscissa which represents the pressure value of the cuff 1 as a variable, and a pulse wave axis 46 constitutes the ordinate which represents the peak value of the K. S. signal SK as a variable. In the two-dimensional graph 47 a group of the pressure signals SP and a group of the peak values stored in the memory 14 are plotted to form a distribution representing the relation of the peak value against to pressure variation of the cuff 1, and furthermore at places where the cuff's pressure values appear when the SYSTOLIC PRESSURE and the DIASTOLIC PRESSURE are observed respective marks Δ (triangle) 48, 48 are printed. The foremost and the rearmost K. S. can be discriminated by observing whether any following signals appear or not after elapse of a certain time span.

Finally, as the third stage, steps 10 and 11 are performed herewith, wherein the DIASTOLIC PRESSURE is detected and a drive signal is simultaneously supplied from the CPU 12 to the electromagnetic valve 6 for releasing the same, followed by rapid discharge of air from the cuff 1.

Figure 7:
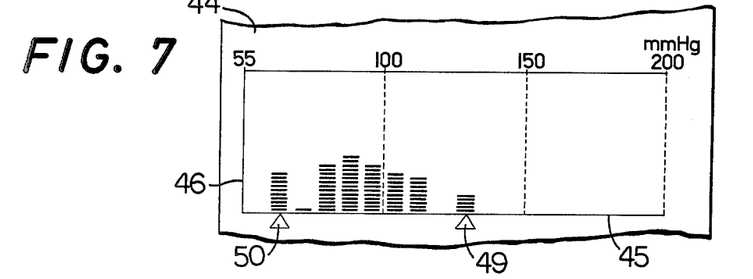
FIG. 7 indicates an abnormal measurement, wherein the data are faulty due to infusion of noises such as MOTION ARTIFACT, etc.

In the event of mingling of noises such as MOTION ARTIFACT with frequencies similar to those of the K. S. signals SK in number and time of generation thereof into the pulse wave sound signals SA, they may be erroneously treated, by escaping the separation by the noise filter 19, as the K. S., either as the systole sound signal SY or as the diastole sound signal SD, in the circuit, leading to misdetermination of the SYSTOLIC PRESSURE and the DIASTOLIC PRESSURE and printing out thereof on the printer 36 as shown in FIG. 7. Since the K. S. is however characteristic in the collective generation and in the description of a gentle and smooth envelope curve, a position with a mark Δ (triangle) 49 indicating the SYSTOLIC PRESSURE somewhat spaced from the group of the peak values and another position with a mark Δ 50 indicating the DIASTOLIC PRESSURE disconnectedly separated from the peak distribution group and showing an unusually high value provides sufficient basis for judging the inappropriateness of the measurement of the SYSTOLIC PRESSURE and the DIASTOLIC PRESSURE.

Even such mingling of noises, such as MOTION ARTIFACT similar to the K. S. in number and generation timing of the frequencies, which is beyond treatment in the circuit only, can be easily excluded in this embodiment from the obtained data, because the existence of erroneously mingled noises can be automatically judged. This method of judgement and exclusion of the error data largely contributes to enhancing the reliability of the blood pressure measurement. When the method is applied to continuous measurement of the blood pressure for knowing a timewise varying trend, output indications in the type of graph 47 which is parallelly deployed will be very helpful for the purpose, because it enables the grasp of the trend by a visibly deployed pattern without using any calculation. Besides, when an output measure such as a dot printer which makes the data visible as a graph style is adopted, this embodiment is very convenient for being utilized for the indication of pulse signals SAA such as in an electrocardiogram, not being limited to the measurement of the K. S., and particularly good for perceiving occurrence of arrhythmia by the pulse shape.

Another embodiment of this invention which is based on the oscillometric method will be described next. In the description similar portions and operations to those in the previous embodiment will be omitted only by allotting the same numerals and signs thereto. In the block diagram of FIG. 8, a pressure signal SP is supplied to a filter 54 as a pulse wave detector, and a pulse wave signal SH as a pressure oscillation of the cuff 1 discriminated by the filter 54 is supplied to a peak hold circuit 25, wherein the peak value of the pulse wave signal SH is maintained just like in the previous embodiment. The peak value is in turn supplied to a CPU 12 via an A/D converter.

Figure 9:
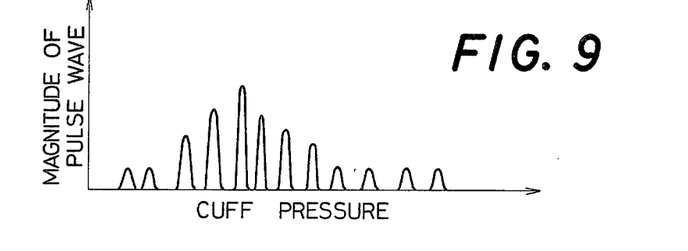
FIG. 9 is a graph showing the generating condition of pulse wave, i.e. pressure vibration in the cuff observed in the embodiment in FIG. 8.
Figure 10:
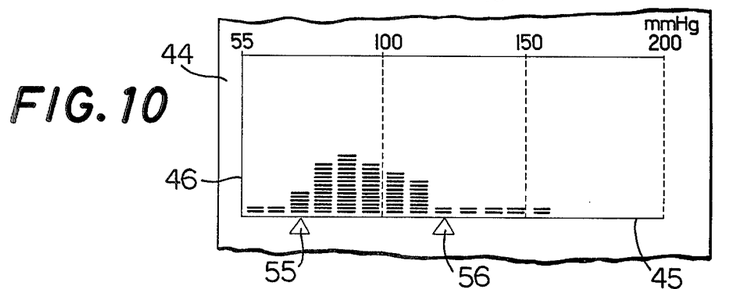
FIG. 10 is an indication of data, in respect of the embodiment in FIG. 8, output on a sheet of printer.

When therefore pulse wave which is represented by the pulse wave signal SH takes place as shown in FIG. 9, pressure in the cuff 1 at a time point 55, where the rate of increase of the peak value representing the magnitude of the pulse wave according to a not shown program is maximum, is measured as the SYSTOLIC PRESSURE; and pressure in the cuff 1 at a time point 56, where the rate of decrease of the peak value is maximum, becomes the DIASTOLIC PRESSURE. Just like the operation in the previous embodiment, a graph showing the distribution of the pulse wave magnitude and the time points with triangle marks 55, 56 of the blood pressure measurement is printed out on a dot printer as a two-dimensional coordinates graph, wherein a pulse wave axis 46 representing the magnitude of the pulse wave signal SH constitutes the ordinate and a pressure axis 45 representing the pressure in the cuff 1 constitutes the abscissa.

The above description was concerned only to a couple of embodiments with reference to the drawing. This invention can be, however, applied to various modified and altered cases for those skilled in the art without departing from the spirit of the appended claims.

For example, the graph 47 indicating the relation between the pressure of the cuff 1 and the peak value of the K. S. is not limited to a bar-graph type, but may be of line graph type. And the mark 48 attached to the pressure value axis 45 may be, in addition to that of triangular, of other shape.

The output device or means is required of only capability of making the graph 47. It can be, not being limited to the dot printer 36, an aggregate of illuminable lamps arranged in matrix, an electron tube such as CRT, etc.

The digital indication of the SYSTOLIC PRESSURE and the DIASTOLIC PRESSURE is allowed to be an LED type separately disposed from the graph 47 as can be seen in the prior art, not necessarily limited to the above described way, i.e., indication within the graph 47 or simultaneous printing out of the data in the vicinity of the same.

The pressure setting circuit 10, the A/D converter 11, 26, and the peak hold circuit 25 in the above embodiments may be respectively changed to a digital circuit. Moreover, all of those can be wholly incorporated into a microcomputer together with the CPU 12, the OR circuit 27, the AND circuit 28, and the memories 14, 31.

The blood pressure measurement is performed in the embodiments in the course of pressure descending in the cuff. It can be however changed to a measurement in the course of gradual ascending of pressure of the cuff 1, which is meritorious in shortening of compressing time duration applied to the arm of the subject person.

The just mentioned measurement has another advantage, that is to say, since the pressure signal SP representing the pressure in the cuff 1 contains pulse wave components from the compressed blood vessel without including the K. S. variation of the peak value or actual value representing the intensity of the pulse wave can be directly used for the blood pressure measurement. In this method the pulse wave sound detector (microphone) 13, the pulse filter 16, the systole filter 17, and the diastole filter 18, etc., may be eliminated.

The above description is all concerned to only some of the embodiments. It is needless to say that this invention is by no means limited to those embodiments.

What is claimed is:

1. A method of measuring blood pressure of a subject through use of a cuff placed over a body part of the subject to apply a cuff pressure to a blood vessel in the body part, said method comprising the steps of:
   varying said cuff pressure as a function of time, and detecting said cuff pressure and a pulse wave produced in association with said blood vessel, to take repeated readings of said cuff pressure and said pulse wave;
   determining and recording a first and a second level of said cuff pressure as a systolic and a diastolic blood pressure, respectively, by analyzing said repeated readings of said cuff pressure and said pulse wave;
   providing a visible indication of values of said repeated readings of the pulse wave as a function of said cuff pressure, in the form of a two-dimensional graph representing said cuff pressure as a first variable along a first axis, and varying magnitudes of said pulse wave as a second variable along a second axis;
   attaching two marks to said graph at positions along said first axis, thereby indicating said first and second levels of the cuff pressure respectively determined as said systolic and diastolic blood pressures; and
   checking the recorded data of said first and second levels of the cuff pressure for validity thereof as to represent said systolic and diastolic blood pressures, by analyzing the positions of said two marks with respect to the indicated readings of the pulse wave magnitudes against a known characteristic of variations in the pulse wave magnitude in relation to the transition of the cuff pressure through the systolic and diastolic pressure levels.

2. A method in accordance with claim 1, wherein said pulse wave is detected in the form of Korotkoff sounds detected through a microphone system.

3. A method in accordance with claim 1, wherein said pulse wave is detected in the form of pressure oscillation of said cuff.

4. A method in accordance with claim 1, wherein said two-dimensional graph is constituted by a plurality of graphic indicia disposed along said first axis and representing the values of said repeated readings of said pulse wave along said second axis.

5. A method in accordance with claim 4, wherein said graphic indicia consists of a plurality of bars printed on a medium.

6. An apparatus for measuring blood pressure of a subject, comprising:
   means including a cuff placed over a body member of said subject for applying a cuff pressure to a blood vessel in the body member;
   means for gradually varying said cuff pressure;
   detector means for detecting said cuff pressure and generating pressure signals each representing a varying level of the detected cuff pressure, and for detecting a pulse wave associated with said blood vessel and generating pulse wave signals each representing a varying magnitude of the detected pulse wave;
   peak hold means for maintaining peak values of the wave form represented by said pulse wave signals;
   a memory for storing, synchronously with generation of said pulse wave signals, said peak values as the magnitudes of said pulse wave, and the corresponding levels of said cuff pressure represented by said pressure signals;
   output means for providing a visible indication of said peak values as a function of said cuff pressure, in the form of a two-dimensional graph representing said cuff pressure along a first axis and said peak values along a second axis;
   data processing means for controlling said output means to provide said visible indication, and determining and measuring a first and a second level of said cuff pressure as a systolic and a diastolic blood pressure, respectively, based on said peak values and said cuff pressure levels stored in said memory, said data processing means further controlling said output means to attach two marks to said graph at positions along said first axis to indicate said first and second levels of the cuff pressure which have been respectively determined as said systolic and diastolic blood pressures, whereby said graph and said two marks provide visible information for checking said first and second levels for validity thereof as measurement data to represent said systolic and diastolic blood pressures, said checking being made with reference to a known characteristic of variation in the pulse wave magnitude in relation to the transition of the cuff pressure through the systolic and diastolic pressure levels.

7. An apparatus in accordance with claim 6, wherein said detector means comprises a microphone for picking up pulse wave sounds from said body member and generating pulse wave sound signals representing said pulse wave sounds, said peak hold means maintaining the peak values of Korotkoff sounds included in said pulse wave sound signals.

8. An apparatus in accordance with claim 6, wherein said detector means comprises a filter for detecting pressure oscillation of said cuff and generating pulse wave signals representing the magnitude of said pressure oscillation, said peak hold means maintaining the peak values of said pulse wave signals.

9. An apparatus in accordance with claim 6, wherein said output means comprises a printer which prints said two-dimensional graph and said two marks on a paper medium.

10. An apparatus in accordance with claim 6, wherein said two-dimensional graph is constituted by a plurality of graphic indicia disposed along said first axis and representing the magnitudes of said pulse wave along said second axis.

11. An apparatus in accordance with claim 10, wherein said graphic indicia consists of a plurality of bars printed on a medium.

* * * * *